United States Patent
Fried et al.

(10) Patent No.: US 12,048,513 B2
(45) Date of Patent: Jul. 30, 2024

(54) ESTIMATING AND CONTROLLING SKIN TEMPERATURE WITH LOW TEMPERATURE THERMAL CONDUCTIVITY RECHARGER

(71) Applicant: Medtronic, Inc., Minneapolis, MN (US)

(72) Inventors: Andrew T. Fried, St. Paul, MN (US); Douglas W. Brown, Shakopee, MN (US); Robert M. Schulzetenberg, Columbia Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 494 days.

(21) Appl. No.: 17/324,737

(22) Filed: May 19, 2021

(65) Prior Publication Data

US 2021/0386296 A1   Dec. 16, 2021

Related U.S. Application Data

(60) Provisional application No. 63/037,641, filed on Jun. 11, 2020.

(51) Int. Cl.
*A61B 5/01*   (2006.01)
*A61B 5/00*   (2006.01)
*H02J 7/00*   (2006.01)
*H02J 50/00*   (2016.01)

(52) U.S. Cl.
CPC .............. *A61B 5/01* (2013.01); *A61B 5/0008* (2013.01); *H02J 7/00032* (2020.01); *H02J 7/00309* (2020.01); *H02J 50/005* (2020.01); *A61B 2560/0214* (2013.01); *A61B 2562/0271* (2013.01); *A61B 2562/166* (2013.01)

(58) Field of Classification Search
CPC ..................................... H02J 50/005
USPC ............................................. 320/153
See application file for complete search history.

(56) References Cited

U.S. PATENT DOCUMENTS

| | | | |
|---|---|---|---|
| 9,225,190 B2 | 12/2015 | Labbe et al. | |
| 10,322,288 B2 * | 6/2019 | Kallmyer | A61N 1/3787 |
| 10,485,478 B1 * | 11/2019 | Mirov | A61B 5/14551 |
| 2005/0075694 A1 | 4/2005 | Schmeling et al. | |
| 2009/0024347 A1 | 1/2009 | Chandra et al. | |
| 2013/0154553 A1 | 6/2013 | Steele | |

(Continued)

FOREIGN PATENT DOCUMENTS

| | | |
|---|---|---|
| RU | 2666793 | 12/2017 |
| WO | WO 2018/046156 | 3/2018 |

(Continued)

OTHER PUBLICATIONS

International Search Report and Written Opinion from PCT Application PCT/US2021/036355 dated Aug. 31, 2021, 10 pgs.

(Continued)

*Primary Examiner* — Yalkew Fantu
(74) *Attorney, Agent, or Firm* — Husch Blackwell LLP

(57) ABSTRACT

Devices and methods described herein facilitate rapid wireless recharging, while reducing risk of injury, damage, or discomfort caused by heat generated during recharging. The embodiments described herein are useful in a variety of context, including for IoT devices, personal electronics, electric vehicles, and medical devices, among others.

16 Claims, 11 Drawing Sheets

(56) References Cited

U.S. PATENT DOCUMENTS

| | | |
|---|---|---|
| 2013/0278226 A1* | 10/2013 | Cong ............... G01J 5/07 |
| | | 320/150 |
| 2015/0073509 A1 | 3/2015 | Kallmyer et al. |
| 2018/0126177 A1* | 5/2018 | Scott ............... A61F 7/0085 |
| 2018/0159361 A1 | 6/2018 | Cong et al. |
| 2018/0345025 A1 | 12/2018 | Stinauer et al. |
| 2019/0190296 A1 | 6/2019 | Paralikar et al. |

FOREIGN PATENT DOCUMENTS

| | | |
|---|---|---|
| WO | WO 2018/084978 | 5/2018 |
| WO | WO 2019/118001 | 6/2019 |

OTHER PUBLICATIONS

Lord Fulfillment, "Potting and Encapsulant Materials". Accessed Dec. 13, 2019, 12 pgs.

Antonacci, "Cooling down your wireless power receiver". EDN Network, Jul. 25, 2012, 7 pgs.

Zhao et al., "Studies in RF Power Communication, SAR, and Temperature Elevation in Wireless Implantable Neural Interfaces", PLoS ONE 8(11): e77759. doi: 10.1371/journal.pone.0077759, Nov. 6, 2013, 11 pgs.

Wolf, "Indwelling Neural Implants: Strategies for Contending with In Vivo Environment". Excerpt of Chapter 3. CRC Press 2008, 20 pgs.

* cited by examiner

ESTIMATING AND CONTROLLING SKIN TEMPERATURE WITH LOW TEMPERATURE THERMAL CONDUCTIVITY RECHARGER

RELATED APPLICATION

This application claims the benefit of U.S. Provisional Application No. 63/037,641 filed on Jun. 11, 2020, the entirety of which is incorporated herein by reference.

FIELD

The present technology is generally related to wireless recharging. In embodiments, wireless recharging of devices or systems can be managed to regulate heat transferred to adjacent systems, and wireless rechargers can be designed to reduce total heat transferred from the recharger to adjacent structures.

BACKGROUND

Wireless recharging is increasingly important in systems across a variety of technical fields. For example, wirelessly recharged phones or other devices are increasingly common, and other systems such as electric cars or Internet of Things (IoT) devices arranged throughout a residence or business require a supply of electric charge that is inconvenient to provide via wired connections. One field in which wired electrical power is particularly difficult to provide is that of implantable medical devices, which can serve to provide medical treatment for years without the opportunity for easy wired recharging.

At a basic level, wireless recharging requires only two parts: an emitter and a receiver. The emitter provides a varying electromagnetic field, which is harnessed by the receiver to create a charge current. The charge current can be used either to directly do some work (such as providing medical treatment) or to charge or recharge a battery coupled to the receiver.

Converting electromagnetic signal into charge current inherently generates some level of heating. Often, operation of the device that is being charged or recharged generates additional heating. Depending on the device, there can be maximum safe temperatures. In addition to damaging the device itself, surrounding materials or environment may be heat sensitive. This is especially true for medical devices, in which overheating can cause injury or discomfort to the patient. Likewise, the recharger itself generates heat as current is routed through a coil to create the charging field.

Conventionally, overheating has been modeled to determine a safe charge current level in emitters and receivers that, even in the most extreme conditions expected to occur, is unlikely to cause damage to the device or surrounding environment. Based on such modeling, the total charge current can be capped at what is determined to be a safe threshold. This is not ideal, however, for many systems because the design is constrained from high charge current levels and accompanying fast charging times due to the cap, even in circumstances where faster charging would not be injurious or damaging. Often these caps are set quite low because, if they were raised to make charging more time-efficient, the resulting damage or injury would be significant.

For medical devices, a housing or enclosure is typically used to enclose the wireless recharger coil, a printed circuit board and other electronics, and a battery. The most restrictive design constraint of the enclosure is often the constituent materials' thermal properties as they relate to skin temperature. The enclosure material should desirably keep skin temperature as low as possible during recharging the implant. Heat management is not only a safety concern in many implantable medical devices, but is directly related to recharge duration and battery capacity.

Depending upon the complexity of the device and how critical prevention of overheating is, temperature sensors may be included a wireless recharger. Temperature sensors provide more flexibility than would otherwise be available for thermal management, because they can be used, for example, to detect a temperature threshold at which the device or surrounding elements will be damaged if it is heated further.

SUMMARY

In one aspect, a wireless recharger includes an enclosure having specific thermophysical material properties that reduce the potential for heat transfer at an undesirably high rate.

In one embodiment, a wireless recharger includes a charging coil and an enclosure surrounding the charging coil and defining a substantially flat face. The enclosure is made of a material having a thermal conductivity and a specific heat, the enclosure comprising a thermal barrier having a thermal conductivity of the material is less than about 0.5 W/m-° C. and the specific heat of the material is greater than 2300 J/kg-° C.

In some embodiments, the wireless recharger can further comprise a temperature sensor in thermal contact with the face, and opposite the thermal barrier from the charging coil. The enclosure can include a first portion having a substantially smaller thickness orthogonal to the face than a second portion of the enclosure surrounding the first portion. The wireless recharger can further include a battery and a circuit board. The material can be a polymer. The wireless recharger can include an air gap arranged between the charging coil and the substantially flat face. The thermal barrier can be formed separately from the enclosure. The thermal barrier can have a toroidal shape.

In another embodiment, a wireless recharge system can include a wirelessly rechargeable device comprising a receiving coil. The system can include a wireless recharger comprising a charging coil configured to generate an alternating electromagnetic signal directed to the receiving coil, and an enclosure comprising a thermal barrier, the enclosure surrounding the charging coil and defining a substantially flat face, the enclosure thermal barrier comprising a material having a thermal conductivity and a specific heat. The thermal conductivity of the material can be less than about 0.5 W/m-° C. and the specific heat of the material is greater than 2300 J/kg-° C.

The wireless recharge system can further comprise a temperature sensor in thermal contact with the face. The enclosure can include a first portion having a substantially smaller thickness orthogonal to the face than a second portion of the enclosure surrounding the first portion. The wireless recharger can further comprise a battery and a circuit board. The material can be a polymer. The wireless recharge system can include an air gap arranged between the charging coil and the substantially flat face. The thermal barrier can be formed separately from the enclosure. The recharge coil can be in contact with the enclosure at less than 50% of a surface area thereof.

The details of one or more aspects of the disclosure are set forth in the accompanying drawings and the description

DETAILED DESCRIPTION

Figure 1A:
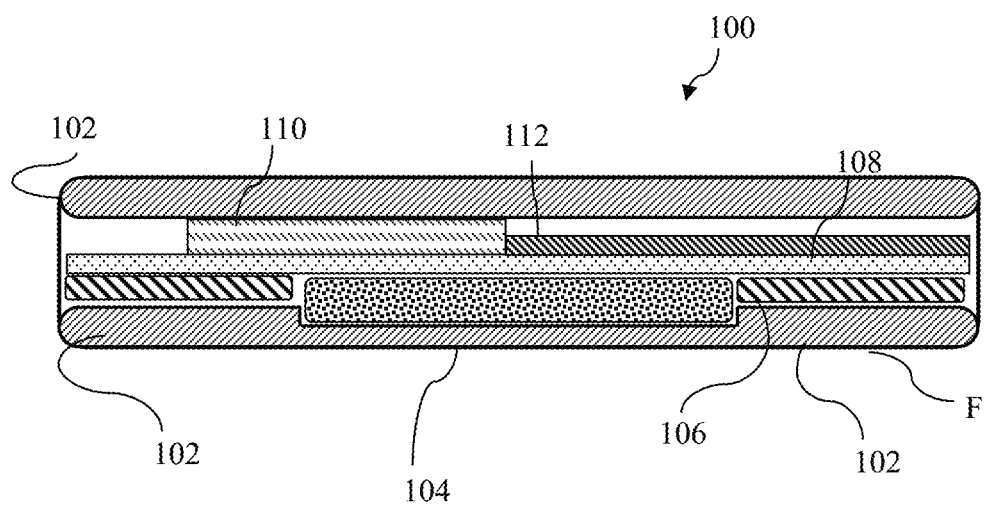
FIG. 1A is a simplified cross-sectional view of a wireless recharger, according to an embodiment.

Systems and methods disclosed herein improve upon conventional wireless recharge systems by reducing thermal transfer to a surrounding environment, and modeling the resulting heat transfer to avoid overheating the device or surrounding environment. Enclosures are described herein that reduce the thermal transfer from a charging coil to a surrounding environment, such that charging may be conducted more rapidly without generating a corresponding spike in temperature in the ambient environment, such as on a user's skin. Rather, the high thermal resistivity of the enclosure results in a smoothing of the heat transfer over more time. When used with rechargeable, implantable medical devices, this smoothing provides for faster charging sessions that do not exceed the instantaneous or longer-term heat limits for safety and comfort. As a result, devices described herein and the methods for using them can result in charging that is faster and less likely to cause injury or damage than equivalent devices without such thermal enclosures and corresponding thermal management systems.

Materials used to form the enclosures described herein are those that have desirable combinations of specific heat, density, and thermal conductivity that result in the improvements described above. It was found that the product of density and specific heat of any given material that increases the efficacy of that material for smoothing heating in the ambient environment.

FIG. 1 shows a wireless recharger 100 according to an embodiment. Rechargeable device 100 includes an enclosure 102 having a variable thickness along a face F, such that it is thinnest at a portion 104 adjacent an internal coil 106. Coil 106 is backed by ferrite 108 in the embodiment shown in FIG. 1, and is electronically coupled to battery 110 via printed circuit board (PCB) 112.

Wireless recharger 100 could be used to recharge any of a variety of wirelessly rechargeable devices (not shown). For example, wireless recharger 100 could be intended for use in recharging implantable or even implanted medical devices. Wireless recharger 100 can recharge devices by driving a varying electromagnetic field at a receiver coil of the device.

Enclosure 102 holds the components of wireless recharger 100 in, but acts as more than a simple housing. Enclosure 102 provides thermal separation between the device 100 and adjacent structures, which can include a patient's skin (when used as a recharge system for a medical device) or, in other embodiments, other components such as wireless recharge receivers of consumer devices, automobiles, or Internet of Things (IoT) devices.

Portion 104 is a section of the enclosure that is adjacent coil 106. Portion 104 is thinner than the remainder of enclosure 102 along face F and surrounding the portion 104. As such, coil 106 is further (and more thermally separated) from face F than would be possible if it were arranged adjacent to any other portion of enclosure 102. Portion 104 can be, for example, 0.13 cm (0.05 inches) while the remainder of enclosure 102 has a thickness up to about 0.25 cm (0.10 inches). In other embodiments, the thickness of portion 104 (i.e., the distance perpendicular to face F) can be about half of the thickness of the remainder of enclosure 102 along face F.

Face F is substantially flat in FIG. 1 so that it can be positioned adjacent a patient. It should be understood that depending upon the location of use of wireless recharger, different contours of face F can be used. It is not necessary for face F to be perfectly flat, and slight curvatures would still be acceptable or even desirable for recharging of implanted devices in portions of the body that are not flat.

Enclosure 102, including portion 104, can be formed of a material that is substantially transmissive to wireless signal at the expected frequency of a recharge and/or communication signal emitted by coil 106. Additionally, enclosure 102, including portion 104, is formed of a material that acts to prevent thermal transfer from coil 106 to face F.

It has been discovered that several structural, thermally conductive polymers have thermal properties appropriate for use as an outer housing of the recharger as described above. In particular, polymers have been discovered that have high thermal conductivity while remaining electrically insulating. In one such embodiment the polymer material has a thermal conductivity of about 1.4 W/mK in plane and 0.5 W/mK through plane. In one embodiment a thermally conductive thermoplastic elastomer can be used to encapsulate the recharge coil. Table 1, below, includes a non-comprehensive list of identified and given to the design team for modeling evaluation. The options cover a range of base materials, thermal conductivities, and mechanical properties (impact strengths).

TABLE 1

Thermally Conductive Polymeric Material Options for Screening Activities for the Wireless Recharger

| Supplier | Material | Base material | Thermal conductivity through plane (W/mK) | Thermal conductivity in plan (W/mK) | Impact Strength (Notched) (ft-lb/in) |
| --- | --- | --- | --- | --- | --- |
| Sabic | LNP KONDUIT PX11311 | PA 6 | 1.2 | 2.1 | 0.8 |
| Sabic | LNP KONDUIT PX11313 | PA 6 | 1.4 | 1.8 | 0.5 |
| Sabic | LNP KONDUIT DTK22 | PC | 0.6 | 2 | 2.8 |
| RTP | 200 TC-I-25 | PA 6/6 | 1.5 | 5 | 0.5 |
| RTP | 299 X 137151A | PA 6/6 | 1.2 | 10 | 0.5 |
| RTP | 299 X 137092D | PA 6/6 | 0.75 | 2.5 | 0.8 |
| RTP | 199 X 103410A | PP | 0.65 | Not given | 6 |

Table 1 is not an exclusive list, but merely provides examples of the types of materials that could be used in forming embodying materials and devices. These materials and others, as well as combinations thereof, have been incorporated into devices to determine which materials facilitate the highest charging rates without exceeding skin temperature requirements for contact with humans.

It has been surprisingly found, contrary to the initial expectations, that high thermal conductivity is not critical to limiting the skin and coil temperatures. Instead, the low thermal conductivity and high specific heat combination of the material gave the lowest maximum skin temperature and average coil temperature.

One particular material that exhibited the desired levels of thermal conductivity and electrical resistance was found by combining materials based on impact-grade nylon 6, polycarbonate, and acrylonitrile butadiene styrene (ABS). Such blends were found to exhibit specific heat of about 2500 J/kg-K, with thermal conductivity of 0.2 W/m-K. The specific heat value is per ASTM C351 which provides specific heat at a mean temperature of 60° C. Specific heat of materials at the use temperature of the wireless recharger are closer to the lower specific heat value of 1500 J/kg·K used in the DOE. However, the low specific heat/low thermal conductivity combination in general, and surprisingly, gave better results than low specific heat/high thermal conductivity materials.

Returning to FIG. 1A in particular, ferrite 108 is an optional component of wireless recharger 100 that is arranged along the side of coil 104 that is opposite from face F. The relative positions of coil 106 and ferrite 108, as well as the position of coil 106 at thicker portion 104 of enclosure, are arranged to promote increased field strength in the up-and-down direction with respect to the orientation of the page in FIG. 1. In particular, ferrite 108 causes the field shape and strength to be directed downward with respect to the orientation shown in FIG. 1.

Battery 110 and PCB 112 are also arranged within wireless recharger 100 according to the embodiment shown in FIG. 1, though in alternative embodiments the wireless recharger 100 could be powered by a wired connection. Battery 110 provides electrical potential, and PCB 112 (or other circuitry, in other embodiments) creates an appropriate signal to drive coil 106 to create a varying electromagnetic field for recharging.

The arrangement of coil 106 at portion 104 can provide several benefits. First, coil 106 is arranged close to face F (e.g., 0.1 inch or less from face F), such that signal strength at face F (and below it) is sufficient for good electromagnetic emission. Second, in some embodiments telemetry or other communications can be useful between the wireless recharger 100 and the device being recharged. In such embodiments, it can be useful for coil 106 or a separate communications coil (not shown) to be within range of the recharged device to facilitate near-field communication.

Wireless recharger 100 should ideally be kept at low temperature at face F in order to avoid injury, damage, or discomfort. When recharging a medical device, for example, wireless recharger 100 can be positioned with face F on a patient's body for a sustained period of time. Typical recharge session durations could be 30 to 90 minutes, for example. Some wireless recharge sessions are accomplished by wearing a battery-powered recharger (such as the one depicted in FIG. 1) in a holster, sling, pouch, or other garment that keeps face F positioned on the patient's body, with coil 106 arranged generally facing a receiver coil of the implanted device. There are several generally exclusive goals for wireless recharging. For example, recharge session time should ideally be minimized, as should heating at face (which corresponds with faster recharging speeds). Likewise, the amount of the material that makes up enclosure 102 and especially portion 104 should be reduced, while thermal transfer from coil to the face F (which corresponds to thinner portions 104) should be increased.

As described herein, use of novel materials accomplishes improvements that address all of these seemingly-contradictory goals. In general, thermal energy is known to transfer to a human body by both direct conduction and blood perfusion according to the Pennes bioheat transfer equation:

$$(\rho c)_t \frac{\partial T_t}{\partial t} = k_t \nabla^2 T_t + (\rho c)_b \omega (T_{core} - T_t) + S_{gen} \quad \text{Eq. 1}$$

where $\rho$ refers to material density, k refers to thermal conductivity, $c_p$ refers to specific heat, and T refers to temperature, $\omega$ is the local tissue-blood perfusion rate (i.e., the volumetric flow rate of blood in the tissue adjacent to face F), and the subscripts t and b refer to properties of tissue and blood, respectively. $S_{gen}$ refers to metabolic heat generation, but it often not a significant contributor to heat generated during wireless recharge and so it is omitted below.

Depending upon the patient, a wireless recharger 100 used to recharge an implanted medical device can vary significantly. The thickness of skin, fat, and muscle varies not only from patient to patient, but also between different regions of the body and even possibly as a function of time at a given location for any given patient. These values are shown in Table 2, below, for one particular patient at a specific location:

TABLE 2

| Component | Thickness (mm) | Density ρ (kg/m³) | Specific heat $c_p$ (J/kg-° C.) | Conductivity k (W/m-° C.) | Perfusion ω (m³/s-m³) |
|---|---|---|---|---|---|
| Skin | 1.98 | 1100 | 3390 | 0.29 | 0.0018 |
| Fat | 30 | 960 | 2300 | 0.20 | 0.000425 |
| Muscle | 20 | 1040 | 3800 | 0.41 | 0.0004 |

Heat conduction in the recharger affects the total amount of heating at face F. The general heat conduction equation for the components of the recharger 100 itself is:

$$(\rho c)_i \frac{\partial T_i}{\partial t_i} = k_i \nabla^2 T_i + \dot{Q}_{electric,i} \quad \text{Eq. 2}$$

where the subscript i refers to components of the wireless recharger 100. Among the components of the recharger, only the copper coil experiences significant heating. As a consequence, $Q_{electric,i}$ is zero except with respect to the coil.

Enclosure 102 can be made of any of a variety of materials that are safe for skin contact and transmissive to electromagnetic signal, as described above. Typically, enclosure 102 is a plastic overmold, made from a material such as the ones listed in Table 3, below

TABLE 3

| Material | Specific Heat (J/kg-° C.) | Conductivity (W/m-° C.) |
|---|---|---|
| DuPont Performance Polymers ZYTEL ® FN727 NC010A PA6-F | 2700 | 0.19 |
| Sabic PX08322 (Polyimide 6) | 1670 | 2.10 |
| RTP 299 X 91020 A Z (Polypropylene) | 1920 | 0.60 |

TABLE 3-continued

| Material | Specific Heat (J/kg-° C.) | Conductivity (W/m-° C.) |
|---|---|---|
| Cycoloy C2950 (Polycarbonate/ABS) | 2000 | 0.20 |
| Impact Grade Nylon 6 | 2510 | 0.42 |
| Lubiloy RF203AXH (Polyimide 6/6) | 1700 | 0.23 |
| High Density Polyethylene (HDPE) | 2000 | 0.47 |
| CoolPoly D8120 | 1300 | 0.77 |

By testing actual skin temperature during recharge, the effect of specific heat, thermal conductivity, and their statistical interaction was determined. Specific heat has a negative effect on temperature while thermal conductivity has a positive effect. The amount of effect is approximately 0.4 to 0.6° C. for both the maximum skin and average coil temperature. Specific heat appears to have greater effect on maximum skin temperature when thermal conductivity is high as shown by non-parallel lines in the Interaction Plot. This is likely because when thermal conductivity is high, heat is delivered faster and so the response is greater. There does not appear to be interactions between the specific heat and thermal conductivity for average coil temperature. Since the coil is located in the center of the assembly, and the top and sides of the assembly are adiabatic, the effect of thermal conductivity on the temperature of the coil is lower than specific heat.

Equations 1 and 2 show that it is the product of density and specific heat (i.e., heat capacity $\rho c$) that controls the solution. Nothing in the equations, however, would give the impression that either of these factors is of greater or lesser importance. Based on the test data corresponding to the materials in Table 2, however, it was found that the magnitude of thermal conductivity is of lesser importance compared to heat capacity when it comes to reducing total overall heat delivered through the material. In particular, the thermal conductivity functions only in a heat delivery role, and not in the absorption of heat.

Figure 1B:
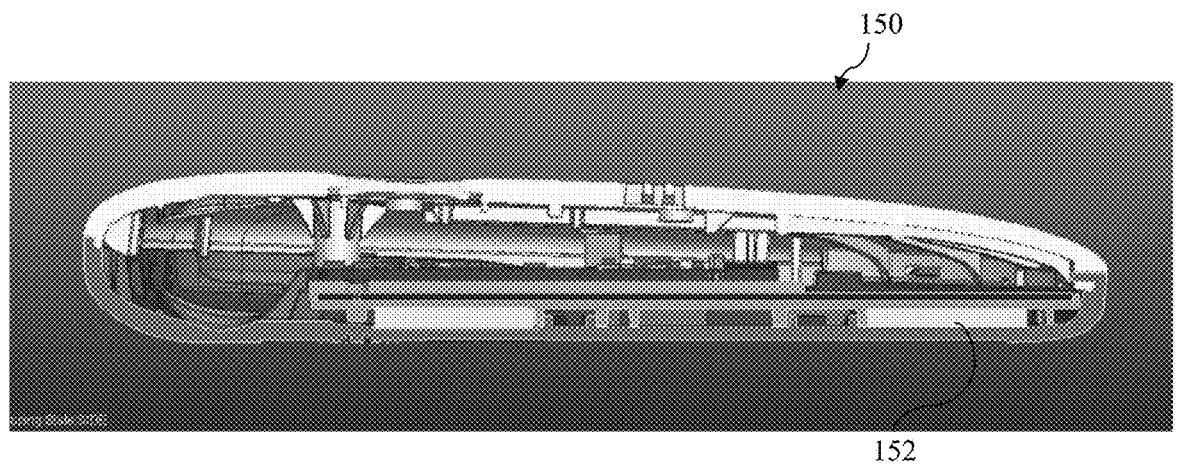
FIGS. 1B-1D are cross-sectional views of a particular embodiment of a wireless recharger.
Figure 1C:
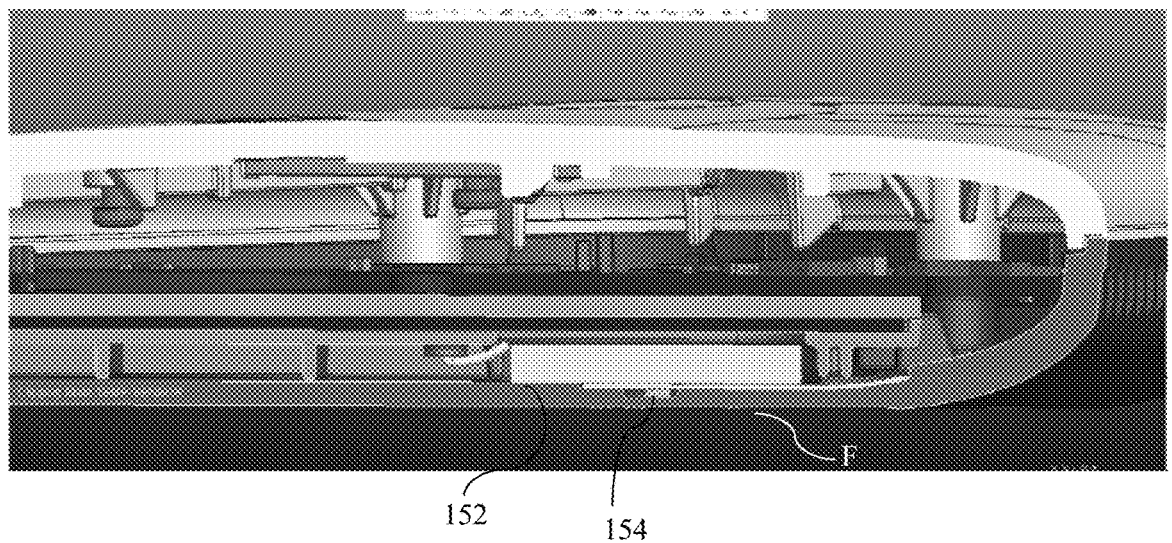
Figure 1D:
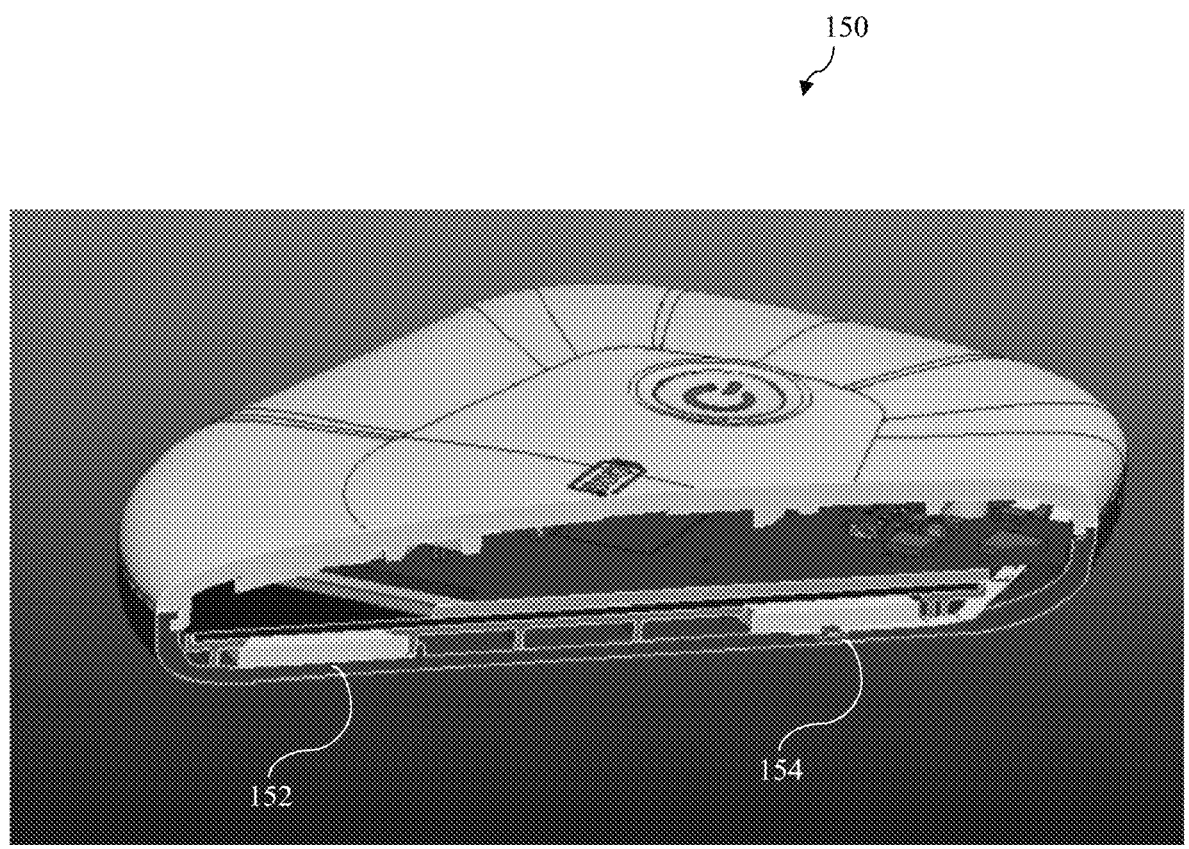

FIG. 1B depicts a cross-section of a device 150, according to an embodiment. Device 150 includes a thermal barrier 152, made from a material similar to those described above with respect to FIG. 1A and Tables 1-3. FIG. 1C shows an enlarged view of the same cross-section as FIG. 1B, further pointing out a temperature sensor 154 arranged between the thermal barrier 152 and the exterior housing and face F, which is similar to the face F of FIG. 1A. FIG. 1D shows an angled cross-section of the same device 150, depicting the way in which the thermal barrier 152 extends across multiple portions of the device 150. In particular, for the device 150 depicted in FIGS. 1B-1D, the thermal barrier 152 is substantially toroidal.

As shown in FIGS. 1B-1D, the toroidal shape of the thermal barrier 152 creates an air gap between the recharge coil and the face F of the enclosure. This increases the thermal resistance since air itself has a very low thermal conductivity. The coil in FIGS. 1B-1D is assembled such that there is a gap or, in alternative embodiments, the coil can contact the enclosure only at limited locations to reduce thermal transfer. In embodiments, the recharge coil is in contact with the enclosure at less than 50% of the surface area thereof.

Figure 2:
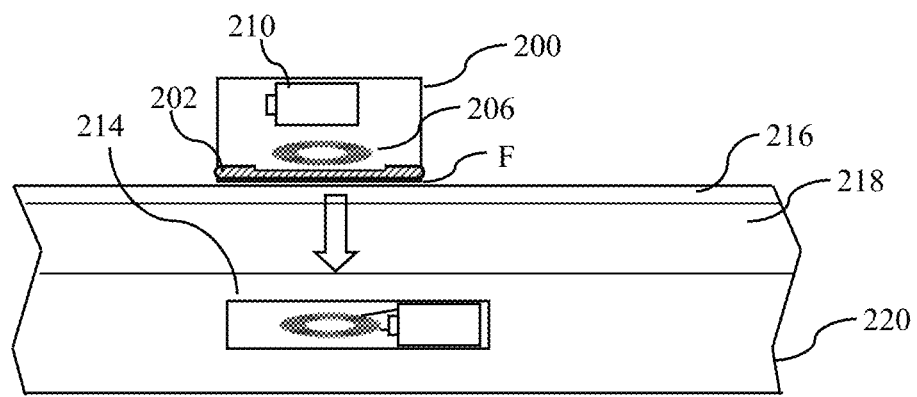
FIG. 2 is a simplified cross-sectional view of a wireless recharge system, according to an embodiment.

FIG. 2 shows a wireless recharger 200, according to an embodiment. Wireless recharger 200 is substantially similar to the wireless recharger 100 described above with respect to FIG. 1, and like components are referred to with like reference numbers, iterated by a factor of 100.

FIG. 2 also shows the implanted device 214 itself, with the wireless recharger 200 arranged such that electromagnetic field produced by coil 206 arrives at a corresponding coil (not labeled) of the device 214, as indicated by the open arrow. Depending upon the device 214 and its intended function, it may be arranged at different depths in the patient. In FIG. 2, skin 216, subcutaneous fat 218, and muscle 220 are depicted, each having different thermal transfer characteristics as described above.

New rechargers (100, 200) are being designed that are smaller and recharge more quickly than those previously available. State of the art rechargers operate at higher frequency (e.g., 100 kHz to about 150 kHz) and, due to their smaller size, are more constrained with respect to the placement of components such as ferrite that can be used to affect field depth and shape. In an embodiment, wireless recharger 200 includes a temperature sensor facing the patient (that is, along face F). Additionally, and contrary to conventional techniques, the material used to form the enclosure 202 has a low thermal conductivity (i.e., high thermal resistance), which leads to a large difference in temperature between the inside and the outside of the wireless recharger 200. As such, more energy can be put into the wireless recharger before the outside at face F gets hot.

Figure 3:
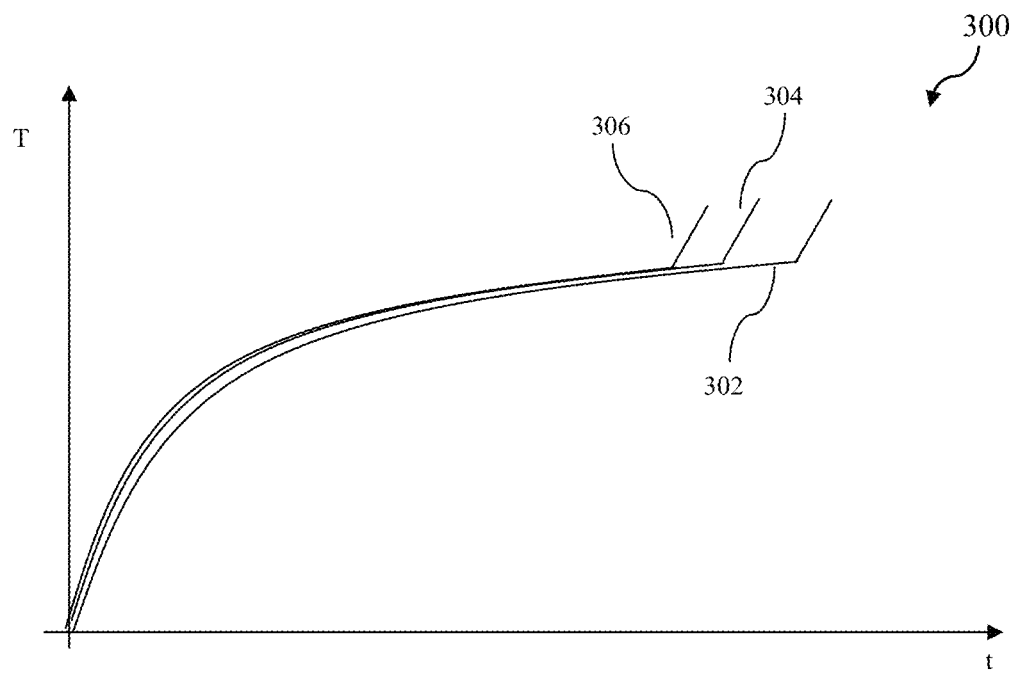
FIG. 3 is a graph of temperature as a function of time for wireless recharge systems, according to three embodiments.

FIG. 3 shows temperature as a function of time for three enclosure materials used on otherwise-identical wireless rechargers. The temperature T shown in FIG. 3 is at the face of the device that is in contact with the patient. As shown in FIG. 3, temperature increases asymptotically at first, and the three curves (302, 304, 306) corresponding to three materials rise substantially at the same rate. The asymptote of these curves is at skin temperature, and heating for the time when these curves (302, 3004, 306) are rising together is primarily based upon the body's heat.

Curves 302, 304, and 306 eventually begin to increase more rapidly. First, curve 306 begins increasing away from 302 and 304; then curve 304 begins increasing away from 302; and finally, curve 302 increases discontinuously and passes the asymptote just like the other two curves 304 and 306. This second phase of heating is caused by heating from within the wireless recharging device itself.

Figure 4:
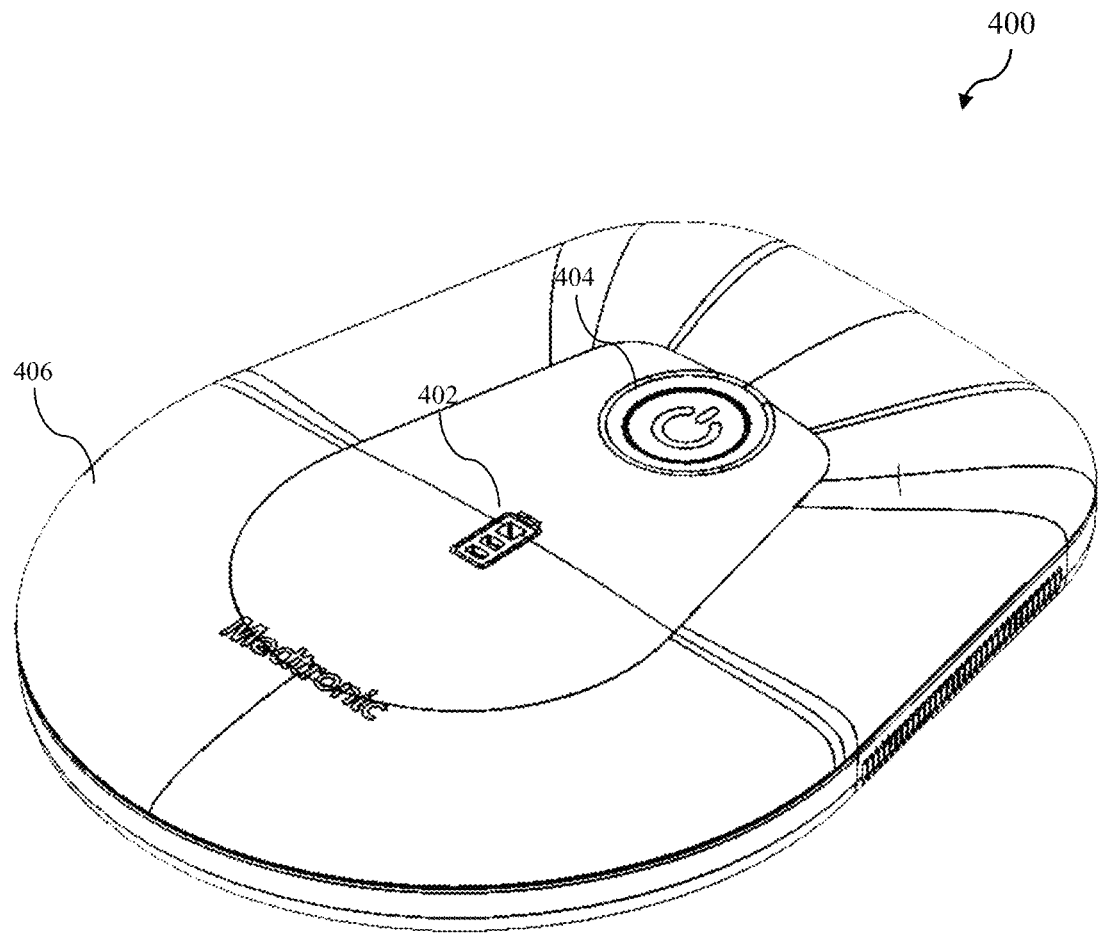
FIGS. 4-9 depict a particular embodiment of a wireless recharger.

FIGS. 4-9 show an embodiment of a wireless recharger 400. FIG. 4 is a top perspective view of a recharger 400 including a display 402, an on/off switch 404, and a housing 406.

Figure 5:
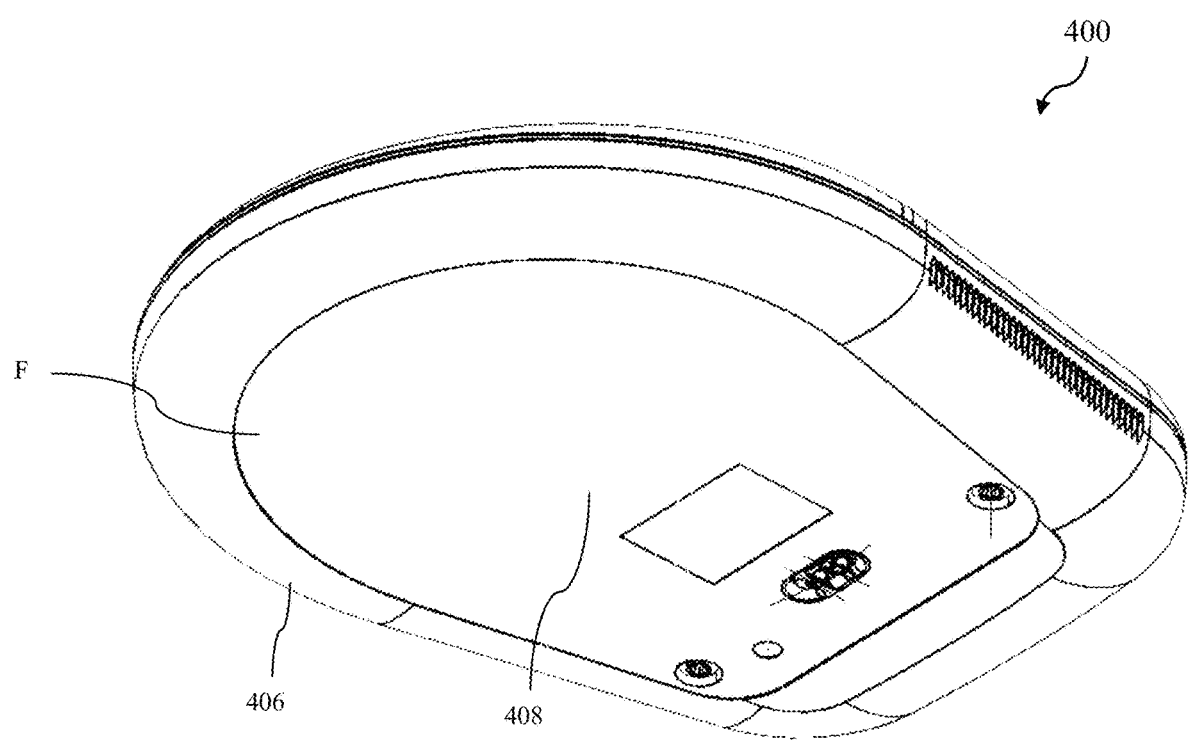

FIG. 5 shows a bottom view of the wireless recharger 400. In use, the bottom surface 408 of the housing 406 is positioned on the patient adjacent to a portion of the body where a medical device has been implanted, in order to provide charging or recharging. Therefore the face F of the bottom surface 408 should generally remain below a preset temperature maximum set either for safety or comfort, or to meet regulatory or other guidelines for heat exposure over various time frames.

Figure 6:
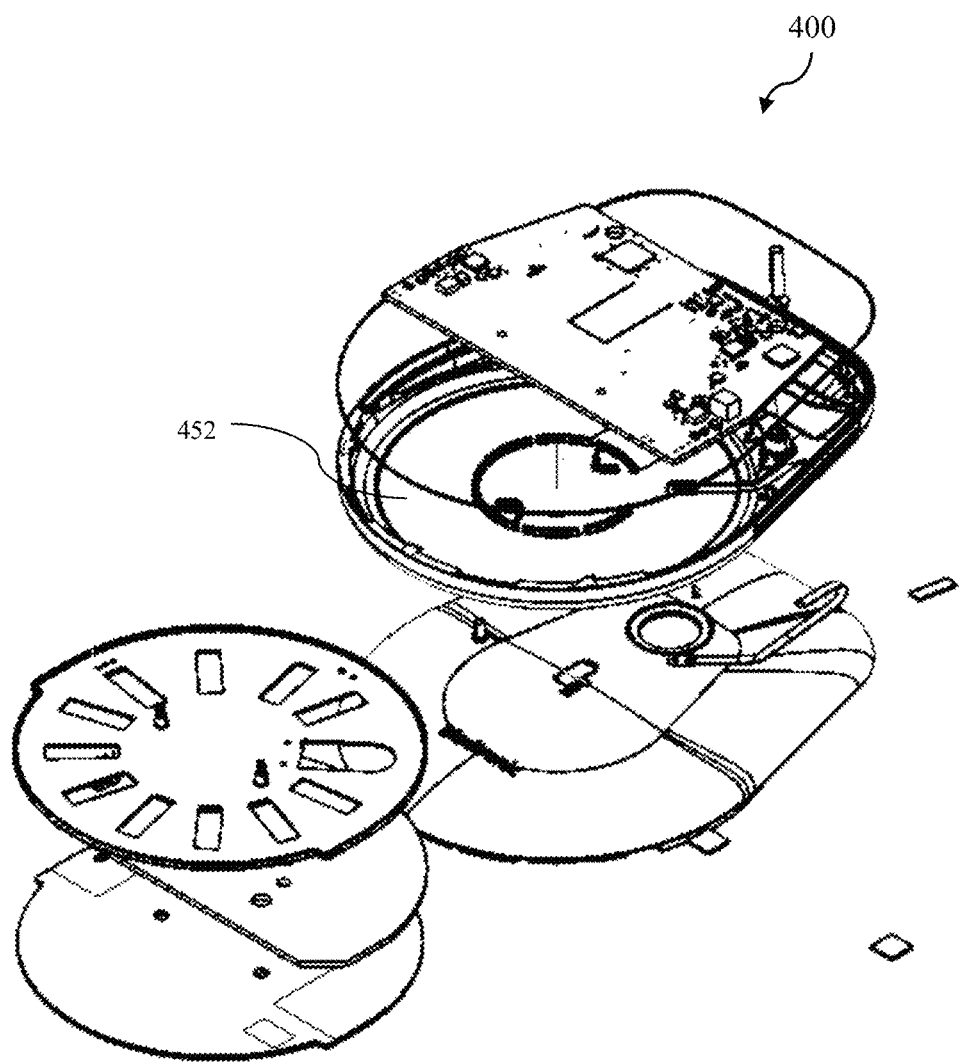

FIG. 6 is an exploded view of the wireless recharger 400 depicting the toroidal thermal barrier 452 therein.

Figure 7:
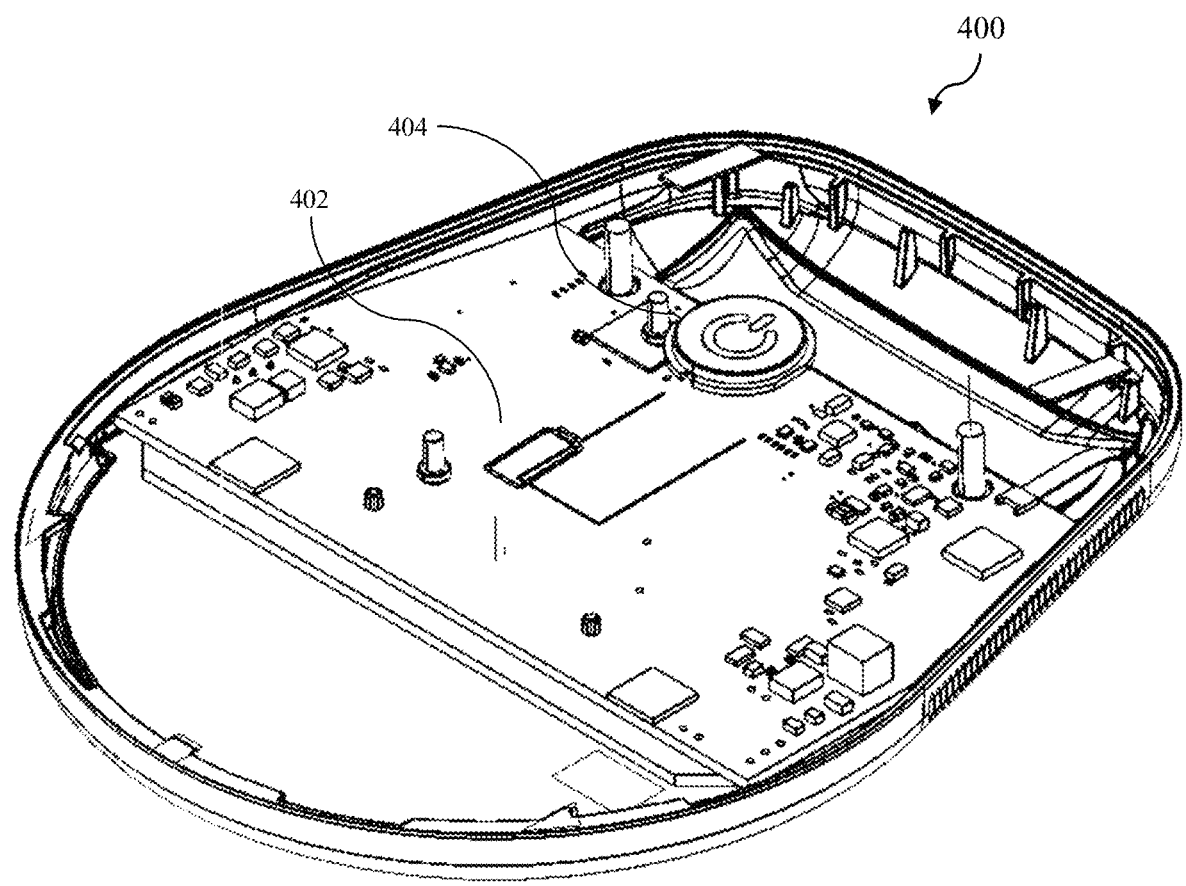
Figure 8:
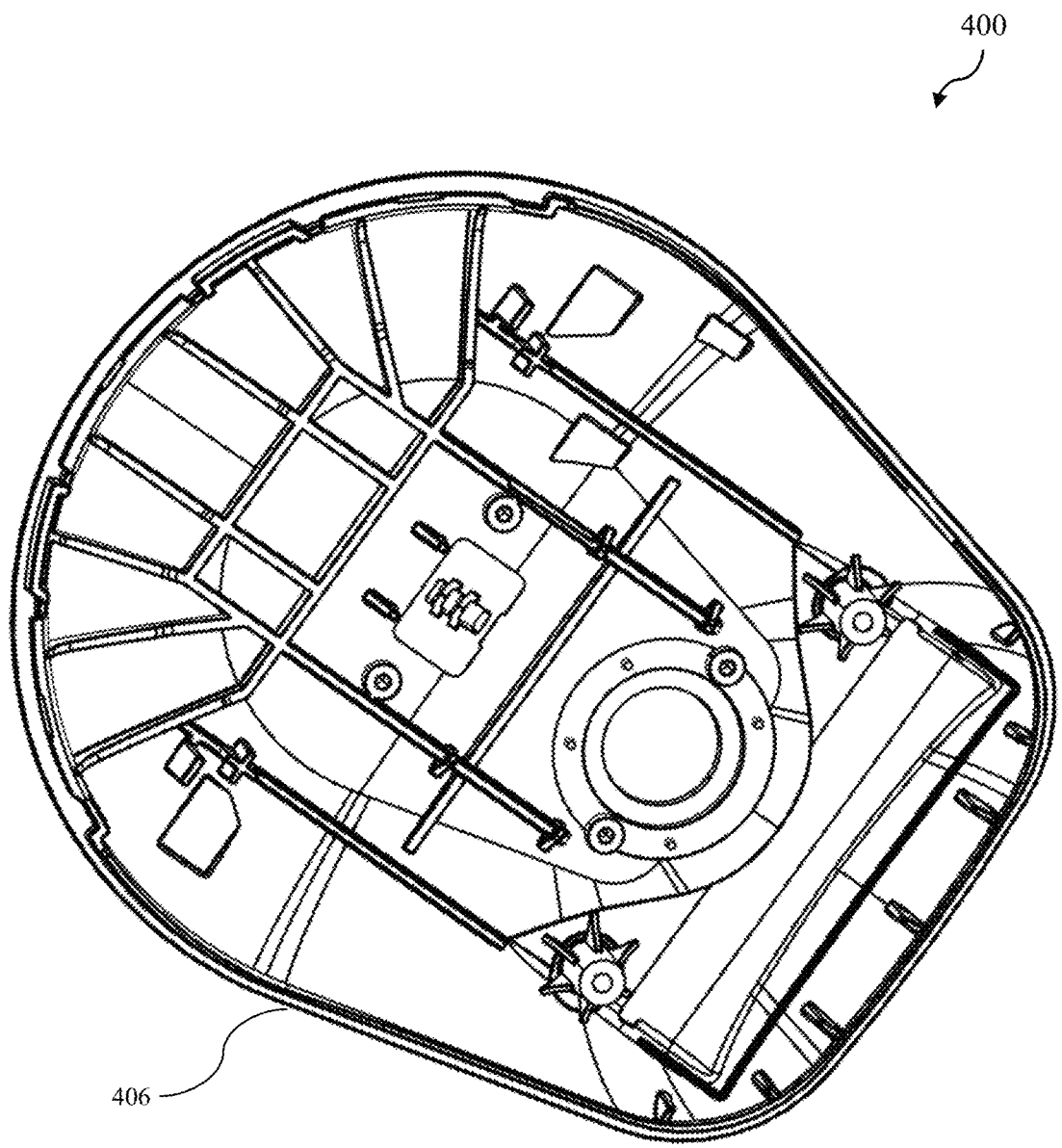
Figure 9:
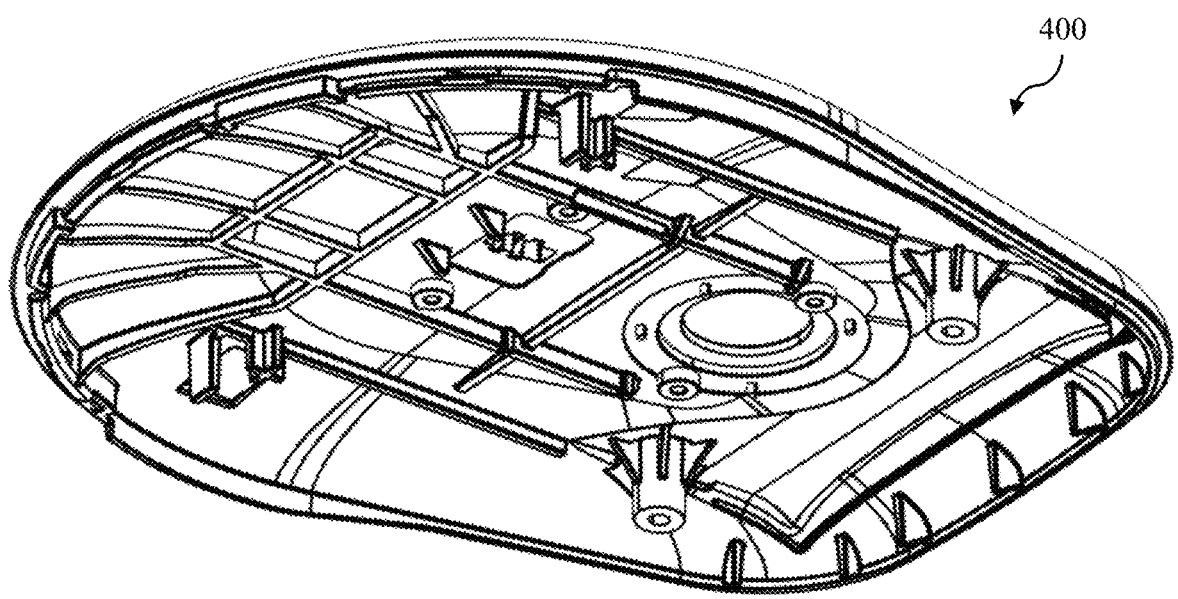

FIG. 7 is an inside view of the interior top side of the wireless recharger 400 depicting the backside of display 402 and on/off button 404, previously depicted. FIGS. 8 and 9 are the equivalent, inside views of the clamshell housing 406 (i.e., the portion at the bottom face 408 depicted in FIG. 5).

For many wireless recharges, the time before this second phase of heating can be an hour or more, so long as appropriately low thermal conductivity materials.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A wireless recharger comprising:
 a charging coil; and
 an enclosure surrounding the charging coil and defining a substantially flat face, the enclosure comprising a material having a thermal conductivity and a specific heat;
 the enclosure comprising a thermal barrier having a thermal conductivity of the material is less than about 0.5 W/m-° C. and the specific heat of the material is greater than 2300 J/kg-° C.

2. The wireless recharger of claim 1, further comprising a temperature sensor in thermal contact with the face, and opposite the thermal barrier from the charging coil.

3. The wireless recharger of claim 1, wherein the enclosure includes a first portion having a substantially smaller thickness orthogonal to the face than a second portion of the enclosure surrounding the first portion.

4. The wireless recharger of claim 1, further comprising a battery and a circuit board.

5. The wireless recharger of claim 1, wherein the material is a polymer.

6. The wireless recharger of claim 1, further comprising an air gap arranged between the charging coil and the substantially flat face.

7. The wireless recharger of claim 1, wherein the thermal barrier is formed separately from the enclosure.

8. The wireless recharger of claim 7, wherein the thermal barrier has a toroidal shape.

9. A wireless recharge system comprising:
 a wirelessly rechargeable device comprising a receiving coil; and
 a wireless recharger comprising:
  a charging coil configured to generate an alternating electromagnetic signal directed to the receiving coil; and
  an enclosure comprising a thermal barrier, the enclosure surrounding the charging coil and defining a substantially flat face, the enclosure thermal barrier comprising a material having a thermal conductivity and a specific heat;
 wherein the thermal conductivity of the material is less than about 0.5 W/m-° C. and the specific heat of the material is greater than 2300 J/kg-° C.

10. The wireless recharge system of claim 9, the wireless recharger further comprising a temperature sensor in thermal contact with the face.

11. The wireless recharge system of claim 9, wherein the enclosure includes a first portion having a substantially smaller thickness orthogonal to the face than a second portion of the enclosure surrounding the first portion.

12. The wireless recharge system of claim 9, wherein the wireless recharger further comprises a battery and a circuit board.

13. The wireless recharge system of claim 9, wherein the material is a polymer.

14. The wireless recharge system of claim 9, further comprising an air gap arranged between the charging coil and the substantially flat face.

15. The wireless recharge system of claim 9, wherein the thermal barrier is formed separately from the enclosure.

16. The wireless recharge system of claim 9, wherein the recharge coil is in contact with the enclosure at less than 50% of a surface area thereof.

* * * * *